(12) United States Patent
Misske et al.

(10) Patent No.: US 10,370,383 B2
(45) Date of Patent: Aug. 6, 2019

(54) PROCESS FOR PREPARING ISOSORBIDE DI(METH)ACRYLATE

(71) Applicant: BASF SE, Ludwigshafen am Rhein (DE)

(72) Inventors: Andrea Misske, Speyer (DE); Friederike Fleischhaker, Ludwigshafen (DE); Christoph Fleckenstein, Freigericht-Somborn (DE); Martin Kaller, Mannheim (DE); Ritesh Nair, Heidelberg (DE); Ulrik Stengel, Birkenau (DE); Mathieu Blanchot, Lambsheim (DE)

(73) Assignee: BASF SE, Ludwigshafen am Rhein (DE)

( * ) Notice: Subject to any disclaimer, the term of this patent is extended or adjusted under 35 U.S.C. 154(b) by 256 days.

(21) Appl. No.: 15/054,506

(22) Filed: Feb. 26, 2016

(65) Prior Publication Data

US 2016/0251371 A1    Sep. 1, 2016

Related U.S. Application Data

(60) Provisional application No. 62/120,922, filed on Feb. 26, 2015.

(51) Int. Cl.
| | |
|---|---|
| *C07D 493/04* | (2006.01) |
| *C09K 8/42* | (2006.01) |
| *C09K 8/44* | (2006.01) |
| *C08F 22/20* | (2006.01) |
| *C09J 4/00* | (2006.01) |

(52) U.S. Cl.
CPC ............ *C07D 493/04* (2013.01); *C08F 22/20* (2013.01); *C09J 4/00* (2013.01); *C09K 8/426* (2013.01); *C09K 8/44* (2013.01)

(58) Field of Classification Search
None
See application file for complete search history.

(56) References Cited

U.S. PATENT DOCUMENTS

| | | | |
|---|---|---|---|
| 3,887,609 A | 6/1975 | Strehlke et al. | |
| 5,288,767 A | 2/1994 | Cramer et al. | |
| 2011/0130582 A1 | 6/2011 | Bette et al. | |
| 2016/0139526 A1* | 5/2016 | Veregin ............... | G03G 9/1133 430/110.2 |

FOREIGN PATENT DOCUMENTS

| | | |
|---|---|---|
| DE | 2 317 226 A1 | 10/1974 |
| DE | 41 31 458 A1 | 3/1993 |
| RU | 2 446 144 C2 | 10/2009 |
| RU | 2 515 985 C2 | 8/2012 |
| WO | WO 2009/080380 A2 | 7/2009 |

OTHER PUBLICATIONS

International Search Report dated May 6, 2016 in PCT/EP2016/053858 filed Feb. 24, 2016 (with English translation of categories of cited documents).

Zhila Vazifehasl, et al., "New Series of Dimethacrylate-Based Monomers on Isosorbide as a Dental Material: Synthesis and Characterization" International Journal of Composite Materials, vol. 3, No. 4, XP55268012, Jan. 1, 2013, pp. 100-107.

* cited by examiner

*Primary Examiner* — Catherine S Branch

(74) *Attorney, Agent, or Firm* — Oblon, McClelland, Maier & Neustadt, L.L.P.

(57) ABSTRACT

A process for preparing isosorbide di(meth)acrylate by transesterifying alkyl (meth)acrylate with isosorbide, comprising the steps of:

(i) reacting alkyl (meth)acrylate with isosorbide in the presence of a catalyst comprising titanium(IV) or zirconium(IV) and a stabilizer in the presence of an azeotroping agent which forms an azeotrope with the alcohol bound in the alkyl (meth)acrylate, (ii) continuously distilling off the azeotrope of azeotroping agent and alcohol, wherein steps (i) and (ii) are conducted simultaneously until the isosorbide has been essentially fully converted, (iii) adding water to the product mixture which comprises isosorbide (meth)acrylate and is obtained in steps (i) and (ii) and removing the hydrolyzate of the catalyst comprising titanium(IV) or zirconium(IV), (iv) distilling unconverted alkyl (meth)acrylate and azeotroping agent out of the product mixture, (v) distilling off water from the product mixture, wherein step (iv) can also be conducted before step (iii) and steps (iv) and (v) can also be conducted in one distillation step.

15 Claims, No Drawings

PROCESS FOR PREPARING ISOSORBIDE DI(METH)ACRYLATE

The invention relates to a process for preparing isosorbide di(meth)acrylate by transesterification of alkyl (meth)acrylate with isosorbide.

E2BADMA (dimethacrylate of bisphenol A alkoxylated with 2 ethylene oxide units in each case) and E3BADMA (dimethacrylate of bisphenol A alkoxylated with 3 ethylene oxide units in each case) are bisphenol A-based dimethacrylates which are used as crosslinkers, for example in coatings and mixtures for drillholes. They are notable for a rapid reaction time which leads to partial load-bearing capacity of 2-pack mixtures even after a short time and attainment of the final tensile strength after a few hours. In addition, they have a high polymer density with a very good cohesion/adhesion ratio, good crystallization resistance with simultaneously low shrinkage and a low tendency to embrittlement, and high wetting power in order to assure good creeping capacity in capillary cracks.

DE 41 31 458 A1 discloses two-pack adhesive compositions for chemical securing technology, comprising a synthetic resin comprising the di(meth)acrylate of an alkoxylated bisphenol and a hardener for the synthetic resin.

For particular applications, bisphenol A-free crosslinkers having a similar profile of properties are being sought.

Isosorbide is a diol based on renewable raw materials and, in structural terms, is an alternative to bisphenol A, since it has a similarly rigid base structure.

One means of preparing di(meth)acrylates from isosorbide is the esterification of isosorbide with (meth)acrylic acid or the transesterification of methyl acrylate, ethyl acrylate or methyl methacrylate with isosorbide in the presence of suitable catalysts. Both OH groups of isosorbide are secondary OH groups having comparatively low reactivity, and the relative reactivities of the two OH groups are additionally very different. Thus, incomplete conversion is to be expected.

DE 2 317 226 A1 discloses a method of preparing (meth)acrylic esters from a mixture of $C_{10}$-$C_{18}$ alkanols by transesterification of methyl (meth)acrylate in the presence of titanium alkoxide as catalyst and 2,6-di-tert-butylparacresol (TBC) as stabilizer. This method is carried out in the presence of activated carbon. Once the reaction has ended, water is added to hydrolyze the titanium alkoxide to titanium hydroxide/oxide which adsorbs onto the activated carbon. The solid is filtered off and the reaction product is subjected to a steam distillation.

WO 2009/080380 discloses a method of preparing methacrylates from $C_6$-$C_{22}$ alcohols by transesterification of methyl (meth)acrylate with the appropriate alcohols in the presence of titanium alkoxide as catalyst. Example 1 comprises reacting methyl methacrylate with 2-ethylhexanol in the presence of hydroquinone monomethyl ether (MEHQ) as stabilizer and tetraisopropyl titanate as catalyst. An azeotropic mixture of methanol/methyl methacrylate is distilled off here. Once unconverted methyl methacrylate has been distilled off, the 2-ethyihexyl methacrylate comprising catalyst is subjected to a purifying distillation under reduced pressure (about 30 mbar). This affords 2-ethylhexyl methacrylate in 99.4% purity.

It is an object of the invention to provide a process for preparing isosorbide di(meth)acrylate by transesterification of alkyl (meth)acrylate with isosorbide in which by-products are formed only to a minor degree.

The object is achieved by a process for preparing isosorbide di(meth)acrylate by transesterifying alkyl (meth)acrylate with isosorbide, comprising the steps of:
(i) reacting alkyl (meth)acrylate with isosorbide in the presence of a catalyst comprising titanium(IV) or zirconium(IV) and a stabilizer in the presence of an azeotroping agent which forms an azeotrope with the alcohol bound in the alkyl (meth)acrylate,
(ii) continuously distilling off the azeotrope of azeotroping agent and alcohol, wherein steps (i) and (ii) are conducted simultaneously until isosorbide has been essentially fully converted,
(iii) adding water to the product mixture which comprises isosorbide di(meth)acrylate and is obtained in steps (i) and (ii) and removing hydrolyzates of the catalyst comprising titanium(IV) or zirconium(IV),
(iv) distilling unconverted alkyl (meth)acrylate and azeotroping agent out of the product mixture,
(v) distilling off water from the product mixture,
wherein step (iv) can also be conducted before step (iii) and steps (iv) and (v) can also be conducted in one distillation step.

It has been found that, surprisingly, transesterification of alkyl (meth)acrylate with isosorbide in the presence of a catalyst comprising titanium(IV) or zirconium(IV) forms isosorbide di(meth)acrylate in high yields.

By complete removal of the methanol or ethanol formed as coproduct from the reaction mixture, the target product is obtained in high purity.

The content of by-products in the product obtained after step (v) is preferably <4% by weight. By-products are particularly the isosorbide mono(meth)acrylates. In addition, the product obtained after step (v) may comprise unconverted isosorbide. This is not a by-product. In general, the isosorbide content of the product obtained after step (v) is up to 2% by weight, preferably up to 1% by weight. In addition, the product obtained after step (v) may also comprise traces of azeotroping agent, alkyl (meth)acrylate and water. These are likewise not by-products and may be present in the product obtained after step (v) in total amounts of up to 2% by weight, preferably up to 1% by weight.

The amount of all the secondary components (including by-products, isosorbide, azeotroping agent, alkyl (meth) acrylate and water) in the product obtained after step (v) is generally up to 6% by weight, preferably up to 4% by weight.

Suitable alkyl (meth)acrylates are the $C_1$-$C_4$-alkyl (meth) acrylates. In general, methyl (meth)acrylate or ethyl (meth) acrylate is used, with release of methanol or ethanol as alcohols in the transesterification reaction.

The reaction of alkyl (meth)acrylate with isosorbide is effected in the presence of a catalyst comprising titanium (IV) or zirconium(IV). Suitable catalysts comprising titanium(IV) or zirconium(IV) are the Ti(IV) and Zr(IV) tetraalkoxides of linear or branched $C_1$-$C_6$ alcohols, preferably the tetraisopropoxides, tetrabutoxides and the metalate of the reactant alcohol used or mixtures thereof. Metalates substituted by different alcohols or by acetylacetone are also possible.

The reaction of alkyl (meth)acrylate with isosorbide is additionally effected in the presence of one or more stabilizers (polymerization inhibitors). Examples of suitable stabilizers are N-oxides (nitroxyl or N-oxyl radicals, i.e., compounds bearing at least one N—O group), for example 4-hydroxy-2,2,6,6-tetramethylpiperidine N-oxyl, 4-oxo-2,2, 6,6-tetramethylpiperidine N-oxyl, 4-acetoxy-2,2,6,6-tetramethylpiperidine N-oxyl, 2,2,6,6-tetramethylpiperidine N-oxyl, bis(1-oxyl-2,2,6,6-tetramethylpiperidin-4-yl) sebacate, 4,4',4"-tris(2,2,6,6-tetramethylpiperidine N-oxyl) phosphite or 3-oxo-2,2,5,5-tetramethylpyrrolidine N-oxyl; mono- or polyhydric phenols which may bear one or more alkyl groups, for example alkylphenols, for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones, for example hydroquinone, hydroquinone monomethyl ether, 2-methylhydroquinone or 2,5-di-tert-butylhydroquinone; hydroxyphenols, for example catechol (1,2-dihydroxybenzene) or benzoquinone; aminophenols, for example p-aminophenol; nitrosophenols, for example p-nitrosophenol; alkoxyphenols, for example 2-methoxyphenol (guaiacol, catechol monomethyl ether), 2-ethoxyphenol, 2-isopropoxyphenol, 4-methoxyphenol (hydroquinone monomethyl ether), mono- or di-tert-butyl-4-methoxyphenol; tocopherols, for example a-tocopherol and 2,3-dihydro-2,2-dimethyl-7-hydroxybenzofuran (2,2-dimethyl-7-hydroxycoumaran), aromatic amines, for example N,N-diphenylamine or N-nitrosodiphenylamine; phenylenediamines, for example N,N'-dialkyl-p-phenylenediamine where the alkyl radicals may be the same or different and each independently consist of 1 to 4 carbon atoms and may be straight-chain or branched, for example N,N'-dimethyl-p-phenylenediamine or N,N'-diethyl-p-phenylenediamine, hydroxylamines, for example N,N-diethylhydroxylamine, imines, for example methyl ethyl imine or methylene violet, sulfonamides, for example N-methyl-4-toluenesulfonamide or N-tert-butyl-4-toluenesulfonamide, oximes such as aldoximes, ketoximes or amide oximes, for example diethyl ketoxime, methyl ethyl ketoxime or salicylaldoxime, phosphorus compounds, for example triphenylphosphine, triphenyl phosphite, triethyl phosphite, hypophosphorous acid or alkyl esters of the phosphorous acids; sulfur compounds, for example diphenyl sulfide or phenothiazine, or mixtures thereof.

Preference is given to hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol and 2-methyl-4-tert-butylphenol and phenothiazine.

Particular preference is given to hydroquinone monomethyl ether (MeHQ) and phenothiazine (PTZ).

Advantageously, oxygen may additionally be used as a polymerization inhibitor.

For further stabilization, an oxygenous gas, preferably air or a mixture of air and nitrogen (lean air), may be present.

The transesterification reaction (steps (i) and (ii)) is generally carried out at a temperature of from 60° C. to 140° C., preferably from 70° C. to 110° C. In the course of this, an azeotrope of azeotroping agent and alcohol is distilled off continuously.

Suitable azeotroping agents which form an azeotropically boiling mixture with methanol or ethanol are, first of all, methyl acrylate and methyl methacrylate and also ethyl acrylate and ethyl methacrylate themselves. Suitable separate azeotroping agents include cyclohexane, methylcyclohexane, benzene, toluene, hexanes and heptanes, and mixtures thereof. Preference is given to methyl acrylate, methyl methacrylate, ethyl acrylate and ethyl methacrylate, and to mixtures of these with n-heptane and cyclohexane. The term azeotroping agent in this context encompasses the reactant itself and any separate solvent additionally used.

In a preferred embodiment, no separate solvent is used as azeotroping agent. In this case, the alkyl (meth)acrylate reactant itself serves as azeotroping agent.

The azeotroping agent may subsequently be replenished in the reactor. For this purpose, the azeotropic mixture of alcohol and azeotroping agent, in a preferred embodiment, is distilled off by means of a suitable column, stirred with water in a mixing vessel and then transferred into a phase separator, wherein the alcohol, generally methanol or ethanol, dissolves in water and the organic phase separates out as the upper layer. The organic phase is preferably returned to the reaction mixture via the top of the column and hence recirculated save for small losses. It is alternatively also possible to add fresh azeotroping agent and work up the azeotroping agent/alcohol mixture in a separate step or to wholly or partly dispense with replenishment of the azeotroping agent.

In general, alkyl (meth)acrylate is used in a stoichiometric excess. Preferably, the excess of methyl (meth)acrylate per hydroxyl group to be esterified is 5 to 500 mol %, more preferably 5 to 200 mol % and especially 50 to 100 mol %.

The catalyst is used in a concentration of 0.1-10 mol % based on the amount of isosorbide used, preferably in a concentration of 0.1 to 5 mol %.

The transesterification may be conducted at atmospheric pressure, but also under elevated pressure or reduced pressure. In general, it is conducted at 300 to 1000 mbar, preferably at 800-1000 mbar (atmospheric pressure=1000 mbar). The reaction time is generally 1 h to 24 hours, preferably 6 to 18 hours. The transesterification (steps (i) and (ii)) can be effected continuously, for example in a stirred tank cascade, or batchwise.

The reaction may be conducted in all reactors suitable for a reaction of this type. Such reactors are known to those skilled in the art. The reaction is preferably effected in a stirred tank reactor.

The batch can be mixed using any desired apparatuses, for example stirring apparatuses. The mixing can also be effected by feeding in a gas, preferably an oxygen-containing gas.

The alcohol formed, generally methanol or ethanol, is removed continuously or stepwise in a manner known per se by azeotropic distillation in the presence of an azeotroping agent. In addition, methanol may also be removed by stripping with a gas.

In a preferred embodiment, the alcohol is removed from the azeotrope of azeotroping agent and alcohol distilled off in step (ii) by washing with water and the azeotroping agent is recycled into the reaction vessel.

Steps (i) and (ii) are conducted until the isosorbide used has been essentially fully converted to the diester. This is the case when isosorbide has been converted to the diester to an extent of 85%, preferably to an extent of 90% and more preferably to an extent of 95%.

This is followed by steps (iii) and (iv), which may also be carried out in reverse order.

In step (iii), water is added to the product mixture comprising the isosorbide di(meth)acrylate, which results in hydrolysis of the catalyst comprising titanium(IV) or zirconium(IV) to give the corresponding hydroxide. The sparingly soluble hydrolyzate is subsequently removed, for example by filtration or centrifugation.

The filtration can be conducted, for example, with a pressure suction filter. In process engineering terms, for a filtration in the process of the invention, it is possible to use any filtration methods and apparatuses known per se, for example those described in Ullmann's Encyclopedia of Industrial Chemistry, 7th ed., 2013 Electronic Release, chapter: Filtration, 1. Fundamentals and Filtration 2. Equipment. For example, these may be cartridge filters, filter presses, pressure plate filters, bag filters or drum filters. Preference is given to using cartridge filters or pressure plate filters. The filtration can be conducted with or without filtering aids. Suitable filtering aids are filtering aids based on kieselguhr, perlite and cellulose.

Suitable centrifuges and also separators are known to the expert. In process engineering terms, for a centrifugation in the process of the invention, it is possible to use any centrifugation methods and apparatuses known per se, for example those described in Ullmann's Encyclopedia of Industrial Chemistry, 7th ed., 2013 Electronic Release, chapter: Centrifuges, Filtering and Centrifuges, Sedimenting.

In a preferred embodiment, unconverted alkyl (meth) acrylate and water are then subsequently distilled out of the product mixture in the distillation steps (iv) and (v). This distillation is generally effected at a temperature of 40° C. to 100° C., preferably 60° C. to 80° C., and a variable pressure of 2 to 700 mbar. In addition, these components may also be removed by stripping with a gas, preferably an oxygenous gas.

If no separate azeotroping agent is used, steps (iv) and (v) are preferably conducted in a combined distillation step. If a separate azeotroping agent is used, step (iv) is preferably conducted before step (iii).

The distillative removal is carried out, for example, in a stirred tank with jacket heating and/or internal heating coils under reduced pressure.

It will be appreciated that the distillation may also be carried out in a falling-film or thin-film evaporator. To this end, the reaction mixture is passed through the apparatus, preferably repeatedly in circulation, under reduced pressure, for example at 20 to 700 mbar, preferably 30 to 500 mbar and more preferably from 50 to 150 mbar, and a temperature of 40 to 80° C.

An oxygenous gas, preferably air or a mixture of air and nitrogen (lean air), may advantageously be introduced into the distillation apparatus, for example 0.1 to 1, preferably 0.2 to 0.8 and more preferably 0.3 to 0.7m$^3$/m$^3$h, based on the volume of the reaction mixture.

Once steps (iii), (iv) and (v) have been carried out, there remains a product in the form of a bottoms product which is obtained in the purity described hereinabove.

The invention also provides for the use of isosorbide di(meth)acrylate as resin component for two-pack adhesive compositions.

Two-pack adhesive compositions of the invention for chemical securing technology comprise
I. a synthetic resin having a viscosity at 23° C. between 100 and 10 000 (mPa·s), comprising the isosorbide di(meth)acrylate, and
II. a hardener for the synthetic resin.

One component of the adhesive composition of the invention is a synthetic resin having a viscosity (at 23° C.) between 100 and 10 000, preferably 200 to 2000 and especially 500 to 1500 mPa·s, measured in the absence of fillers. It comprises the isosorbide di(meth)acrylate.

The synthetic resin may comprise 2% to 20% by weight of other curable resins, such as polyester, vinyl ester, bismaleimide or epoxy resins, and, for the purpose of the impact modification, 2% to 20% by weight of a thermoplastic such as polyamide or polyester or a rubber.

If accelerators are required for peroxide curing, their position is appropriately together with the resin, i.e. separately from the hardener. Suitable accelerators are: aromatic amines such as N,N-dimethylaniline, N,N-diethylaniline; toluidines and xylidines such as N,N-diisopropylidene-para-toluidine, N,N-dimethyl-p-toluidine, N,N-bis(2-hydroxyethyl)xylidine; and also Co salts, Mn salts, Sn salts or Ce salts, for example cobalt naphthenate, and mixtures of amine accelerators and cobalt accelerators. The accelerators are generally present in the synthetic resin in amounts of preferably 0.5% to 5% by weight.

In general, the supply form of a two-chamber cartridge is chosen. Cartridges used are preferably two-chamber cartridges wherein the larger chamber comprises the resin and the smaller chamber the hardener. The larger chamber has a volume about 5 to 10 times greater than the smaller chamber.

In the chamber comprising the synthetic resin component, it is additionally also possible for fillers to be present. Reinforcing fillers used for the adhesive composition are, for example, quartz, glass, corundum, porcelain, earthenware, heavy spar, light spar, talc and chalk. The fillers are added in the form of sands, flours or specific shaped bodies (cylinders, spheres, etc.), either to the resin solution and/or to the hardener (initiator). The fillers can be used in the form of fibers (fibrous fillers). Preference is given to the globular inert substances (in spherical form), which have much stronger strengthening action.

The hardener is provided in a separate position from the resin. Preferred hardeners are organic peroxides that break down at low temperatures. Of particularly good suitability are benzoyl peroxide and methyl ethyl ketone peroxide, and also tert-butyl perbenzoate, cyclohexanone peroxide, lauryl peroxide and cumene hydroperoxide, and also mixtures of various peroxides.

The peroxides are preferably used in amounts of 0.5% to 10% by weight, preferably of 1% to 5% by weight. The hardeners are appropriately applied to inert fillers, preference being given to quartz sands having particle sizes of 0.5 to 3 mm or of 3 to 6 mm in terms of dimensions.

In the case of foamable adhesive compositions, carbonate is appropriately added to the resin;
the acid component can be introduced into a chamber either together with the hardener or else into a separate, third chamber.

The two-pack adhesive composition of the invention can be used as a plugging compound for securing anchorages in drillholes. Anchorages of this kind have good crack propagation characteristics, low shrinkage stress and excellent adhesion on mineral receiving materials, such as concrete and natural stone, and on foam and cavity blocks.

The invention is more particularly described using the examples which follow.

EXAMPLES

Example 1

A 0.75 L flange reactor having a column, condenser, liquid divider, anchor stirrer and air inlet is initially charged with ethyl acrylate (626 g), MeHQ (0.31 g), phenothiazine (0.31 g) and isosorbide (186 g) and heated up to a bottom temperature of 68° C. with introduction of air while stirring. At a pressure of 300 mbar, 200 g of ethyl acrylate are distilled off. Titanium tetraisopropoxide (7.1 g) is metered in and the mixture is heated up further to bottom temperature 100° C. The reaction mixture is cloudy. Ethyl acrylate and ethanol which has formed are distilled off with full outflow. EA is metered in in portions, in the amounts that correspond to the EA in the distillate. Over the course of the reaction, a further 2.9 g of titanium tetraisopropoxide are metered in.

The bottom temperature rises to 105° C. over the course of the reaction. Bottoms and distillate are sampled at regular intervals to observe the course of the reaction. The pressure is reduced to a pressure of not more than 810 mbar to complete the reaction after a run time of 18 h. The reaction mixture is admixed with 125 mL of water, filtered through a paper filter and concentrated under reduced pressure. The following composition is obtained (GC area %): isosorbide 0%, sum total of isosorbide monoacrylates 3.3%, isosorbide diacrylate target product 96.7%.

Comparative Example 1

A 2 L four-neck flask equipped with a thermometer, stirrer, water trap and air inlet is initially charged with cyclohexane (240 g), isosorbide (503 g), MeHQ (1.23 g), 50% hypophosphorous acid (3.08 g) and Cu(II) acetate solution (5%, 4.6 g). Then methacrylic acid (755 g, stabilized with 200 ppm MeHQ) is metered in, methanesulfonic acid (16.8 g) is added and the mixture is heated up. Water is distilled over at an internal temperature of 84 to 118° C. After 19 h, the reaction is stopped. After cooling, the reaction mixture is extracted with water, with NaOH solution and once more with water. After phase separation, the organic phase is concentrated under reduced pressure. The reaction mixture has the following composition (in GC area %): isosorbide 1.1%, sum total of isosorbide monomethacrylates 22.9%, isosorbide dimethacrylate target product 75.0%

Comparative Example 2

The transesterification is effected in a 1.6 L jacketed reactor equipped with an anchor stirrer, an air inlet, a separating column and a liquid divider. The reflux ratio is 10:1, and later 10:3 (reflux:output), the stirrer speed is 180 rpm and the air introduction rate is 1.5 L/h. This apparatus is initially charged with 175 g of isosorbide, 0.48 g of methylhydroquinone (MEHQ) and 1200 g of methyl methacrylate (MMA, stabilized with 15 ppm of MEHQ) at room temperature. 19.1 g of potassium phosphate are added and the reaction mixture is heated at a bath temperature of 80° C., which is adjusted to 100° C. over the course of the reaction. A pressure of 400 mbar (abs.) is established and an azeotrope of methanol and MMA is distilled off continuously, in the course of which the bottoms temperature rises from 75° C. to 82° C. After the reaction has ended, the product is filtered through a paper filter and the reaction mixture is concentrated under reduced pressure. The reaction mixture has the following composition (in GC area %): isosorbide 0%, sum total of isosorbide monomethacrylates 4.3%, isosorbide dimethacrylate target product>85%

Comparative Example 3

A 4 L flange reactor equipped with a column on top (Sulzer CY packing), cooler, liquid divider, cross-beam stirrer, air inlet and an apparatus for washing the organic phase having a downstream phase separator and automatic recycling of the organic phase is initially charged with heptane (400 g), methyl methacrylate (2740 g), MeHQ (14.6 g), dimethyltin dichloride (52.4 g), 30% sodium methoxide solution in methanol (18.32 g) and isosorbide (967 g), and heated up to a bottom temperature of 95° C. with introduction of air while stirring. Once the mixture has started to boil, a reflux ratio of 6:4 is established. The amount of wash water is matched continuously to the amount of distillate present. The bottom temperature rises to 103° C. over the course of the reaction. Bottoms are sampled at regular intervals to observe the course of the reaction. After 23 h, the following bottoms composition is obtained (GC area %): isosorbide 1.25%, sum total of isosorbide monomethacrylates 24.3%, isosorbide dimethacrylate target product 72.7%

The invention claimed is:

1. A process for preparing an isosorbide di(meth)acrylate by transesterifying an alkyl (meth)acrylate with isosorbide, comprising:
   (i) reacting an alkyl (meth)acrylate with isosorbide in the presence of a catalyst comprising titanium(IV) or zirconium(IV) and a stabilizer in the presence of an azeotroping agent which forms an azeotrope with alcohol bound in the alkyl (meth)acrylate,
   (ii) continuously distilling off the azeotrope of azeotroping agent and alcohol, wherein (i) and (ii) are conducted simultaneously until isosorbide has been essentially fully converted, to obtain a product mixture comprising an isosorbide (meth)acrylate,
   (iii) adding water to the product mixture comprising the isosorbide (meth)acrylate obtained in (ii) and removing a hydrolyzate of the catalyst comprising titanium(IV) or zirconium (IV),
   (iv) distilling unconverted alkyl (meth)acrylate and azeotroping agent out of the product mixture comprising the isosorbide (meth)acrylate, and
   (v) distilling water out of the product mixture comprising the isosorbide (meth)acrylate,
   wherein (iv) can be conducted before (iii), and (iv) and (v) can be conducted in one distillation operation.

2. The process according to claim 1, wherein the azeotroping agent is the alkyl (meth)acrylate.

3. The process according to claim 1, wherein the azeotroping agent is a separate solvent other than the alkyl (meth)acrylate.

4. The process according to claim 3, wherein the azeotroping agent is selected from the group consisting of n-heptane and cyclohexane.

5. The process according to claim 1, wherein (iv) and (v) are conducted in a combined distillation step.

6. The process according to claim 1, wherein the alkyl (meth)acrylate is methyl or ethyl (meth)acrylate.

7. The process according to claim 1, wherein the catalyst comprises titanium(IV) tetraisopropoxide.

8. The process according to claim 1, wherein the stabilizer is selected from the group consisting of hydroquinone monomethyl ether and PTZ.

9. The process according to claim 1, wherein the alcohol is removed from the azeotrope of azeotroping agent and alcohol distilled off in (ii) by washing with water and the azeotroping agent is recycled into a reaction vessel.

10. The process according to claim 1, wherein, after (v), an isosorbide di(meth)acrylate having a content of secondary components of <4% by weight is obtained.

11. A two-pack adhesive composition for a chemical securing technology, comprising:
   (i) a synthetic resin having a viscosity at 23° C. between 100 and 10,000 mPa·s, comprising isosorbide di(meth)acrylate, and
   (ii) a hardener for the synthetic resin.

12. The two-pack adhesive composition of claim 11, wherein the synthetic resin has a viscosity at 23° C. between 200 and 2000 mPa·s.

13. The two-pack adhesive composition of claim 11, wherein the synthetic resin has a viscosity at 23° C. between 500 and 1500 mPa·s.

14. The two-pack adhesive composition of claim 11, wherein the synthetic resin further comprises from 2 to 20% by weight of a further curable resin selected from the group consisting of polyester resins, vinyl ester resins, bismaleimide resins, and epoxy resins.

15. The two-pack adhesive composition of claim 11, wherein the synthetic resin further comprises from 2 to 20% by weight of an impact modifier selected from the group consisting of polyamides, polyesters, and rubbers.

* * * * *